US008828391B2

(12) United States Patent
Denis et al.

(10) Patent No.: US 8,828,391 B2
(45) Date of Patent: Sep. 9, 2014

(54) METHOD FOR EGFR DIRECTED COMBINATION TREATMENT OF NON-SMALL CELL LUNG CANCER

(75) Inventors: Louis Denis, Wiesbaden (DE); Robert Michael Lorence, Bethesda, MD (US); Mehdi Shahidi, Sutton (GB); Flavio Solca, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/471,500

(22) Filed: May 15, 2012

(65) Prior Publication Data
US 2012/0294867 A1 Nov. 22, 2012

(30) Foreign Application Priority Data
May 17, 2011 (EP) .................................. 11166446

(51) Int. Cl.
*A61K 39/00* (2006.01)
*A61K 39/395* (2006.01)
*C07K 16/28* (2006.01)
*C07K 16/30* (2006.01)
*C07K 14/47* (2006.01)
*A61P 35/00* (2006.01)

(52) U.S. Cl.
CPC ................................ *C07K 16/2863* (2013.01); *A61K 39/39558* (2013.01)
USPC ................ 424/142.1; 424/143.1; 530/388.15; 514/7.5; 514/19.3

(58) Field of Classification Search
None
See application file for complete search history.

(56) References Cited

U.S. PATENT DOCUMENTS

| | | | |
|---|---|---|---|
| 7,019,012 B2 | 3/2006 | Himmelsbach et al. |
| 7,220,750 B2 | 5/2007 | Himmelsbach et al. |
| 7,846,936 B2 | 12/2010 | Hilberg et al. |
| 7,960,546 B2 | 6/2011 | Schroeder et al. |
| 8,067,593 B2 | 11/2011 | Schroeder et al. |
| RE43,431 E | 5/2012 | Himmelsbach et al. |
| 8,188,274 B2 | 5/2012 | Schroeder et al. |
| 2002/0169180 A1 | 11/2002 | Himmelsbach et al. |
| 2002/0173509 A1 | 11/2002 | Himmelsbach et al. |
| 2003/0225079 A1 | 12/2003 | Singer et al. |
| 2005/0043233 A1 | 2/2005 | Stefanic et al. |
| 2005/0085495 A1 | 4/2005 | Soyka et al. |
| 2006/0058311 A1 | 3/2006 | Munzert et al. |
| 2006/0100223 A1 | 5/2006 | Himmelsbach et al. |
| 2007/0027170 A1 | 2/2007 | Soyka et al. |
| 2007/0099918 A1 | 5/2007 | Singer et al. |
| 2007/0185091 A1 | 8/2007 | Himmelsbach et al. |
| 2008/0254040 A1 | 10/2008 | Stefanic et al. |
| 2009/0238828 A1 | 9/2009 | Munzert et al. |
| 2009/0306044 A1 | 12/2009 | Solca et al. |
| 2009/0306101 A1 | 12/2009 | Solca et al. |
| 2009/0306378 A1 | 12/2009 | Schroeder et al. |
| 2009/0318480 A1 | 12/2009 | Solca |
| 2010/0010023 A1 | 1/2010 | Himmelsbach et al. |
| 2010/0069414 A1 | 3/2010 | Himmelsbach et al. |
| 2010/0144639 A1 | 6/2010 | Singer et al. |
| 2011/0039863 A1 | 2/2011 | Hilberg et al. |
| 2011/0046168 A1 | 2/2011 | Himmelsbach et al. |
| 2011/0136826 A1 | 6/2011 | Hilberg et al. |
| 2011/0142929 A1 | 6/2011 | Messerschmid et al. |
| 2011/0171289 A1 | 7/2011 | Stefanic et al. |
| 2011/0207929 A1 | 8/2011 | Schroeder et al. |
| 2011/0207932 A1 | 8/2011 | Schroeder et al. |
| 2012/0107399 A1 | 5/2012 | Barta |
| 2012/0157472 A1 | 6/2012 | Larsen et al. |

FOREIGN PATENT DOCUMENTS

| | | | | |
|---|---|---|---|---|
| WO | 0078735 A1 | 12/2000 | | |
| WO | 0250043 A1 | 6/2002 | | |
| WO | 03094921 A2 | 11/2003 | | |
| WO | 2004096224 A2 | 11/2004 | | |
| WO | 2005037824 A2 | 4/2005 | | |
| WO | 2006018182 A1 | 2/2006 | | |
| WO | 2007054550 A1 | 5/2007 | | |
| WO | 2007054551 A1 | 5/2007 | | |
| WO | 2007085638 A1 | 8/2007 | | |
| WO | 2008034776 A1 | 3/2008 | | |
| WO | WO2009030239 | * | 3/2009 | ............. C07K 16/28 |
| WO | 2009147238 A1 | 12/2009 | | |
| WO | 2010081817 A1 | 7/2010 | | |
| WO | 2010085845 A1 | 8/2010 | | |
| WO | 2011003853 A2 | 1/2011 | | |
| WO | 2011069962 A1 | 6/2011 | | |

OTHER PUBLICATIONS

International Search Report and Written Opinion for PCT/EP2012/059098 mailed Jun. 27, 2012.
Regales, L. et al., "Dual targeting of EGFR can overcome a major drug resistance mutation in mouse models of EGFR mutant lung cancer", American Society for Clinical Investigation, vol. 199, No. 10, Oct. 1, 2009, p. 3000-3010.
Reid, A, et al, "Dual inhibition of ErbB1 (EGFR/HER1) and ErbB2 (HER2/neu)", European Journal of Cancer, Pergamon Press, Oxford, GB, vol. 43, No. 3, Feb. 1, 2008, p. 481-489.
Cascone, T. et al, "Epidermal growth factor receptor inhibitors in non-small-cell lung cancer", Expert Opinion on Drug Discovery, Informa Healthcare, London, GB, vol. 2, No. 3, Mar. 1, 2008, p. 335-348.

* cited by examiner

*Primary Examiner* — Elly-Gerald Stoica
(74) *Attorney, Agent, or Firm* — Michael P. Morris; Anthony P. Bottino

(57) ABSTRACT

The present invention relates to a method of treating patients suffering from cancers driven by deregulated Human Epidermal Growth Factor Receptor (HER/Human EGFR), wherein an irreversible tyrosine kinase inhibitor (TKI) is administered according to a continuous regimen based on an average daily dose in the range of 10 to 50 mg and the mAB is co-administered according to a dosing regimen ranging from an average weekly iv dose of 50 to 500 mg/m$^2$ repeated thrice, twice or once a week, once in two weeks, once in three weeks or at least monthly to a patient in need of such treatment.

16 Claims, No Drawings

METHOD FOR EGFR DIRECTED COMBINATION TREATMENT OF NON-SMALL CELL LUNG CANCER

The present invention relates to a method of treating patients suffering from cancers driven by deregulated Human Epidermal Growth Factor Receptor (HER/Human EGFR) such as, but not limited to, non-small cell lung cancer (NSCLC), head and neck squamous cell carcinoma (HNSCC), breast cancer, esophageal cancer, gastric cancer, renal cancer, cervical cancer, ovarian cancer, pancreatic cancer, hepatocellular cancer, malignant glioma, prostate cancer and colorectal cancer (CRC) comprising a flexible and active regimen for combining an irreversible tyrosine kinase inhibitor (TKI) and a Human EGFR targeted monoclonal antibody (mAB), wherein in this method the TKI is administered according to a continuous regimen based on an average daily dose in the range of 10 to 50 mg and the mAB is co-administered according to a dosing regimen ranging from an average weekly intravenous (iv) dose of 50 to 500 mg/m$^2$ repeated thrice, twice or once a week, once in two weeks, once in three weeks or at least monthly to a patient in need of such treatment. The method of treatment of the invention includes treatment of TKI naive patients as well as of patients pretreated with EGFR TKIs, particularly those patients with primary or acquired resistance to treatment with reversible or irreversible TKIs such as gefitinib, erlotinib, 1-(4-(4-(3,4-dichloro-2-fluorophenylamino)-7-methoxyquinazolin-6-yloxy)piperidin-1-yl)prop-2-en-1-one, or salts thereof, EKB-569 (pelitinib), HKI-272 (neratinib), HKI-357, lapatinib, CI-1033 (canertinib), WZ 3146, WZ 4002, WZ 8040 (structures of the three WZ compounds disclosed by Wenjun Zhou et al.: Novel mutant-selective EGFR kinase inhibitors against EGFR T790M, in Nature 2009, Vol. 462, 1070-1074), Icotinib, BIBW 2992 or PF-00299804 (dacomitinib). Furthermore the method of treatment of the invention includes to overcome primary or acquired resistance and prevention or delay of acquired resistance to treatment with (reversible or irreversible) TKIs.

Additional aspects of the invention are pharmaceutical compositions and pharmaceutical kits which include instructions for coadministration of the TKI with the mAB, irreversible TKIs for coadministration with a targeted mAB that prevents the binding of ligands to EGFR and the use of an irreversible TKI for preparation of a pharmaceutical composition comprising an effective amount of the irreversible TKI, together with an instruction for coadministration with the mAB.

BACKGROUND OF THE INVENTION

EGFR is expressed in several solid malignancies, including NSCLC, HNSCC, malignant glioma and colorectal cancer, and abnormal or deregulated EGFR activity is known to contribute to numerous tumorigenic processes. Lung cancer remains the leading cause of cancer death in industrialized countries. Cancers that begin in the lungs are divided into two major types, non-small cell lung cancer and small cell lung cancer, depending on how the cells appear under a microscope. Non-small cell lung cancer (squamous cell carcinoma, adenocarcinoma, and large cell carcinoma) generally spreads to other organs more slowly than does small cell lung cancer. About 75 percent of lung cancer cases are categorized as non-small cell lung cancer (e.g., adenocarcinomas), and the other 25 percent are small cell lung cancer. For patients with advanced disease, chemotherapy provides a modest benefit in survival, but at the cost of significant toxicity, underscoring the need for therapeutic agents that are specifically targeted to the critical genetic lesions that direct tumor growth (Schiller J H et al., N Engl J Med, 346: 92-98, 2002).

Mutations that lead to EGFR overexpression (known as upregulation) or overactivity have been associated with a number of cancers, including lung cancer, anal cancers and glioblastoma multiforme. Mutations, amplifications or misregulations of EGFR or family members are implicated in about 30% of all epithelial cancers. Consequently, mutations of EGFR have been identified in several types of cancer, and has led to the development of anticancer therapeutics directed against EGFR, using two approaches: (1) targeted monoclonal antibodies (mABs) that prevent the binding of ligands to. EGFR, and (2) small molecule tyrosine kinase inhibitors (TKIs) that block the intracellular catalytic activity of the receptor. Skin toxicity characterized by rash or acne-like symptoms and diarrhea of different grades are the most common adverse events of EGFR targeted therapies (Expert Opin. Investig. Drugs (2009) 18(3), 293-300).

The human/mouse chimeric IgG1 mAb cetuximab downregulates EGFR signaling and subsequently inhibits cell proliferation, induces apoptosis and reduces angiogenesis. Cetuximab in combination with chemotherapy has been approved by Health Authorities for the treatment of metastatic colorectal cancer and for the treatment of locally advanced and metastatic head and neck cancer. Cetuximab has also demonstrated little clinical activity as a single agent in patients with advanced NSCLC after prior EGFR TKI therapy (Neal J W, Heist R S, Fidias P, Temel J S, Huberman M, Marcoux J P, Muzikansky A, Lynch T J, Sequist L V; J Thorac Oncol. 2010 November; 5(11):1855-8: Cetuximab monotherapy in patients with advanced non-small cell lung cancer after prior epidermal growth factor receptor tyrosine kinase inhibitor therapy). Panitumumab (VECTIBIX®) is a human IgG2 mAB against EGFR and approved for treatment of metastatic colorectal cancer. Other monoclonals in clinical development are zalutumumab, nimotuzumab, matuzumab and necitumumab.

First generation small molecule HER TKIs include gefitinib (Iressa®) and erlotinib (Tarceva®), both binding reversibly to the EGFR. Gefitinib is indicated in all lines of treatment of advanced NSCLC harbouring EGFR mutations in the tumor and erlotinib is indicated as treatment of advanced NSCLC after prior chemotherapy, but in development in all lines of EGFR mutation positive NSCLC These new drugs directly target the EGFR. Patients have been divided into EGFR positive (EGFR$^+$) and negative (EGFR$^-$), based upon whether a tissue test shows a mutation. EGFR positive patients with tumors harboring EGFR mutations in exons 19 and 21 associated with drug sensitivity (i.e., G719X, exon 19 deletion, L858R, L861Q) have shown an response rate up to 60% which exceeds the response rate for conventional chemotherapy.

Second generation small molecule TKIs have been designed as irreversible EGFR inhibitors which bind irreversibly to EGFR, preferably to cysteine 773 of EGFR. Nonlimiting examples include compounds disclosed in U.S. Pat. No. 6,002,008, U.S. Pat. No. 7,019,012, U.S. Pat. No. 6,251,912, WO 02/50043, WO 2004/074263, WO 2005/037824, WO 2008150118 (specifically the compound of Example 36, 1-(4-(4-(3,4-dichloro-2-fluorophenylamino)-7-methoxyquinazolin-6-yloxy)piperidin-1-yl)prop-2-en-1-one, or salts thereof formed with acidic additives as disclosed in WO 2011155793), EKB-569 (pelitinib), HKI-272 (neratinib), HKI-357, CI-1033 (canertinib), WZ 3146, WZ 4002, WZ 8040 (structures of the three WZ compounds disclosed by Wenjun Zhou et al.: Novel mutant-selective EGFR kinase inhibitors against EGFR T790M, in Nature 2009, Vol. 462, 1070-1074), BIBW 2992 or PF-00299804. BIBW 2992 (afatinib) and PF-00299804 (dacomitinib) are most advanced second generation small molecule TKIs include, both in advanced clinical development for treatment of NSCLC.

More specifically, BIBW 2992, also referred to herein by it's INN afatinib, is known as the compound 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline,

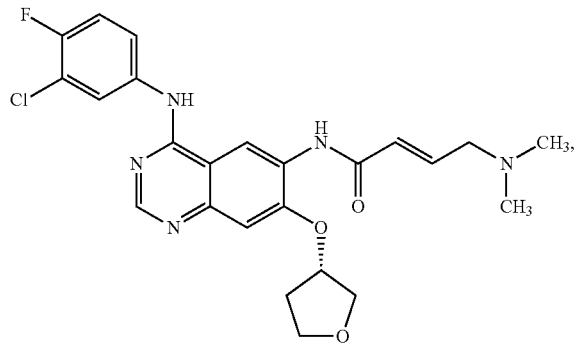 [SMILES: CN(C)C/C=C/C(=O)Nc1cc2c(Nc3ccc(F)c(Cl)c3)ncnc2cc1O[C@H]1CCOC1]

preferably used as a maleate salt BIBW 2992:maleic acid 1:2:

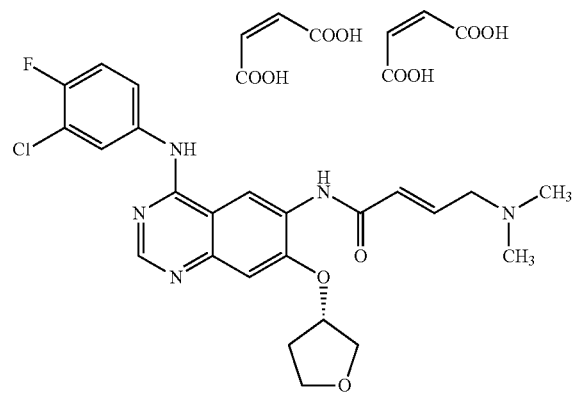 [SMILES: CN(C)C/C=C/C(=O)Nc1cc2c(Nc3ccc(F)c(Cl)c3)ncnc2cc1O[C@H]1CCOC1 ; O=C(O)/C=C\C(=O)O ; O=C(O)/C=C\C(=O)O]

BIBW 2992 is a potent irreversible and selective dual inhibitor of erbb1 receptor (EGFR) and erbB2 (Her2/neu) and erbB4 (Her4) receptor tyrosine kinases which can be administered orally. Furthermore, BIBW 2992 was designed to covalently bind to EGFR and HER2 thereby irreversibly inactivating the receptor molecule it has bound to. This compound, salts thereof such as the dimaleate salt, their preparation as well as pharmaceutical formulations comprising BIBW 2992 or a salt thereof, indications to be treated with BIBW 2992 and combinations including BIBW 2992 are disclosed in WO 02/50043, WO 2005/037824, WO 2007/054550, WO 2007/054551, WO 2008034776 and WO 2009147238.

PF-00299804 is an oral irreversible pan-HER TKI, more specifically an inhibitor of the HER1, 2, and 4 tyrosine kinases. In preclinical studies, PF-00299804 has been shown to inhibit the signaling in both wild-type and mutant EGFR, including forms of NSCLC that are resistant to currently available EGFR inhibitors, such as erlotinib and gefitinib. Preclinical findings suggest that PF-00299804 may be clinically effective against NSCLCs with EGFR or ERB-B2 mutations as well as those harboring the EGFR T790M mutation, which produces resistance to gefitinib and erlotinib (Expert Opin. Investig. Drugs (2010) 19(12): 1503-1514). PF-00299804 (dacomitinib) is the compound N-[4-(3-chloro-4-fluoro-phenylamino)-7-methoxy-quinazoline-6-yl]-3-piperidin-1-yl-acrylamide, disclosed in WO 2005107758 as Examples 2 and 3 with the following structure:

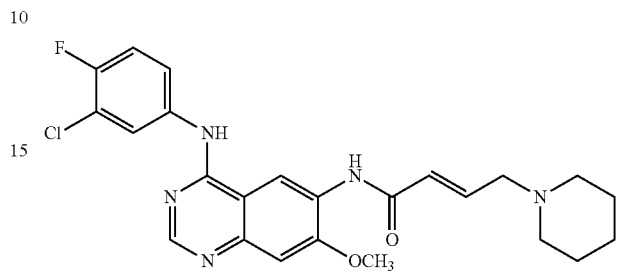

Characteristics of EKB-569 (pelitinib), HKI-272 (neratinib), HKI-357 and CI-1033 are published, e.g. Expert Opin. Investig. Drugs 2009, 18(3), 293-301 provides a review. Development of EKB-569 for treatment of NSCLC has been discontinued several years ago. Others report that HKI-272 can overcome T790M-mediated resistance only at suprapharmacologic concentrations (N. Godin-Heymann et al., The T790M "gatekeeper" mutation in EGFR mediates resistance to low concentrations of an irreversible EGFR inhibitor. Mol. Cancer Ther. 7, 2008:874-879). Remarkably, development of HKI-272 for treatment of NSCLC was discontinued after phase II trial showed that the compound had low activity in patients with prior benefit from TKIs and in TKI-naive patients, potentially because of insufficient bioavailability from diarrhea-imposed dose limitation (L. V. Sequist et al., J. Clin. Onc. 28 (18), 2010, 3076-3083). In contrast to encouraging preclinical results and high potency of HKI-272 these did not translate into clinical benefit, showing the low level of predictability in this field.

Despite initial response in NSCLC patients with EGFR mutations, acquired resistance develops after a median of approximately 12 months. The consensus definition of acquired resistance includes patients who had previous treatment with a single-agent EGFR-TKI (e.g., gefitinib or erlotinib); either or both of the following: a tumor that harbors an EGFR mutation known to be associated with drug sensitivity (i.e., G719X, exon 19 deletion, L858R, L861Q) or objective clinical benefit from treatment with an EGFR-TKI; systemic progression of disease applying RECIST criteria known in the art, while on continuous treatment with EGFR directed treatment for at least 24 weeks.

Response evaluation criteria in solid tumours (RECIST) are described by P. Therasse et al., J Natl Cancer Inst 2000, 92, 205-216; in J. Clin. Oncol. Vol 24, No. 20, 2006, pp 3245-3251; or by Eisenhauer E A, Therasse P, Bogaerts J, Schwartz L H, Sargent D, Ford R, et al., New response evaluation criteria in solid tumours: revised RECIST guideline (version 1.1). Eur J Cancer 2009; 45:228-247. Monitoring tumor progression may be determined by comparison of tumor status between time points after treatment has commenced or by comparison of tumor status between a time point after treatment has commenced to a time point prior to initiation of treatment. Tumor progression may be monitored during treatment visually, for example, by means of radiography, for example, X-ray, CT scan, or other monitoring methods known to the skilled artisan, including palpitation of the cancer or methods to monitor tumor biomarker levels.

In addition to the primary EGFR mutations (associated with erlotinib and gefitinib sensitivity), approximately half of the patients with acquired EGFR-TKI resistance have a second EGFR mutation (T790M) in the ATP-binding pocket of the tyrosine kinase that may alter receptor affinity in favor of ATP. These second mutations enable the cancer cells to continue signaling via mutant EGFR, suggesting that in a proportion of patients with acquired resistance to EGFR-TKIs, tumor growth and proliferation remains dependent on EGFR.

The presence of MET oncogene has been reported as a second sources of resistance (Jackman D, Pao W, Riely G J, Engelman J A, Kris M G, Janne P A et al., Clinical definition of acquired resistance to epidermal growth factor receptor tyrosine kinase inhibitors in non-small-cell lung cancer, J Clin Oncol 2010; 28:357-60).

As of 2010 there was no clinical consensus of an accepted approach to overcome or prevent resistance nor regulatory approval of a specific drug or drug combination in this setting.

There is a significant medical need in the art for a satisfactory treatment of cancer, and specifically epithelial cell cancers such as lung, ovarian, breast, brain, colon and prostate cancers, which incorporates the benefits of EGFR targeted therapy and overcoming the non-responsiveness exhibited by patients' cancers. Thus, the problem underlying the present invention is to establish an improved treatment of patients suffering from epithelial cell cancers, characterized by improved efficacy and improved or at least acceptable tolerability, including the following patient populations (a) TKI naive cancer patients, wherein the improvement includes prevention or delay of resistance to TKI treatment, (b) patients with tumors expressing the wild-type EGFR (described hereinbefore as EGFR), (c) patients with tumors expressing mutated forms of the EGFR (described hereinbefore as EGFR$^+$), (d) patients previously treated with EGFR inhibitors, such as gefitinib or erlotinib afatinib, dacomitinib or others wherein the improvement includes to overcome primary or acquired resistance to EGFR inhibitors, (e) patients with acquired resistance to treatment with TKIs such as gefitinib or erlotinib, afatinib, dacomitinib or others wherein the improvement includes to overcome resistance to TKI treatment, (g) patient populations with primary or acquired resistance caused by T790M (T790M+), wherein the improvement includes to prevent/overcome resistance to TKI treatment, and (h) patient populations with primary or acquired resistance not caused by T790M (T790M−), e.g. by other mechanisms such as MET oncogene or by unknown origin, wherein the improvement includes to prevent/overcome resistance to TKI treatment.

One approach to improve treatment options of NSCLC patients with acquired resistance to gefitinib or erlotinib followed the concept of total receptor blockade by combining a TKI and an anti-EGFR mAB. This is summarized by S. Ramalingam et al., Journal of Thoracic Oncology Vol. 3, Number 3, March 2008, 258-265. The hypothesis was that by the combination it may be possible to achieve simultaneous vertical inhibition of EGFR and enhance abrogation of downstream activity. Residual EGFR activity after exposure to either class of inhibitor alone may allow cancer cells to remain viable, but simultaneously dual inhibition may cause apoptosis. Results in xenograft models support this hypothesis: a synergistic effect has been observed when cetuximab is administered in combination with erlotinib or gefitinib compared with treatment with either agent alone. Cetuximab has been shown to down-regulate EGFR on the cellular surface, potentially enhancing the sensitivity to TKIs. The conclusion was that the combination of cetuximab plus erlotinib seems synergistic in terms of apoptotic activity in vitro, and results in additive tumor growth inhibition in vivo.

Nevertheless, the question is whether these primary results translate in clinical benefit. S. Ramalingam et al. report the results of a phase I study carried out to determine the optimal doses of cetuximab and gefitinib when administered as a combination for patients with advanced/metastatic non-small cell lung cancer (NSCLC) previously treated with platinum-based chemotherapy. Patients with advanced/metastatic NSCLC treated with prior platinum-based chemotherapy received escalating doses of weekly cetuximab (100, 200, and 250 mg/m$^2$, iv) and fixed doses of gefitinib (250 mg/d, PO) until disease progression or unacceptable toxicity. The results reported show that the combination of cetuximab and gefitinib can be safely administered but has only modest activity in advanced/metastatic NSCLC.

Y.Y. Janjigian et al., Clin Cancer Res 2011, 17: 2521-2527, report about a phase I/II trial of cetuximab and erlotinib enrolling 19 patients with lung adenocarcinoma and acquired resistance to erlotinib. Patients with lung adenocarcinoma and clinically defined acquired resistance to erlotinib were treated with erlotinib 100 mg daily, along with cetuximab every 2 weeks in three escalating dose cohorts (250 mg/m$^2$, 375 mg/m$^2$, and 500 mg/m$^2$). The recommended phase II dose was then evaluated in a two-stage trial, with a primary, end point of objective response rate. The recommended phase II dose identified was cetuximab 500 mg/m$^2$ every 2 weeks and erlotinib 100 mg daily. At this dose and schedule, no radiographic responses were seen. In fact, combined EGFR inhibition, with cetuximab 500 mg/m$^2$ every 2 weeks and erlotinib 100 mg daily, had no significant activity in patients with acquired resistance to erlotinib. During the phase II portion of the trial serious tolerability issues occurred. Common grade 2, 3 and 4 toxicities were rash (13 patients, 68%), fatigue (12 patients, 63%) and hypomagnesemia (14 patients, 74%). 31% (6 of 19 patients) discontinued treatment due to intolerable rash.

Both, S. Ramalingam et al. and Y.Y. Janjigian et al., report clinical results obtained with the combination of cetuximab with a reversible (first generation) TKI. In contrast, L. Regales et al., J. Clin. Invest. 119 (10), 2009: 3000-3010, report results obtained with the irreversible (second generation) TKI BIBW 2992 in transgenic mouse lung tumor models that develop lung adenocarcinomas driven by EGFR$^{L858R}$ (sensitive to erlotinib), EGFR$^{T790M}$ (resistant to erlotinib), or EGFRL858R+T790M (resistant to erlotinib) with a focus to evaluate strategies to overcome the most common EGFR TKI resistance mutation, T790M. Other agents mentioned in the investigation were HKI-272 (neratinib) and PF-00299804, but without reporting results. The rationale behind was that preclinical studies published by others (E. L. Kwak, et al., Irreversible inhibitors of the EGF receptor may circumvent acquired resistance to gefitinib. *Proc. Natl. Acad. Sci. U.S.A.* 2005, 102:7665-7670; T. A. Carter et al., Inhibition of drug-resistant mutants of ABL, KIT and EGF receptor kinases. *Proc. Natl. Acad. Sci. U.S.A.* 2005, 102:11011-11016) suggested that second-generation irreversible EGFR inhibitors may be able to overcome T790M-mediated resistance, at least in vitro. Mice bearing tumors harboring EGFR mutations were treated with a variety of anticancer agents, including the irreversible EGFR TKI BIBW 2992 and the EGFR-specific antibody cetuximab. It was found that only the combination of both agents together induced dramatic shrinkage of erlotinib-resistant tumors harboring the T790M mutation.

An open label phase I clinical trial of continuous once daily oral treatment using BIBW 2992 in combination with cetuximab with the primary objective to determine the maximum tolerated dose (MTD) and recommended phase II doses in patients with NSCLC and acquired resistance to erlotinib or gefitinib was disclosed in ClinicalTrials.gov at the priority filing date of the subject patent application, identifier NCT01090011, including the history of changes available via a link to ClinicalTrials.gov archive site. The following qualitative information about the administration regimen was publicly available:

patients to receive medium BIBW 2992 once daily plus biweekly cetuximab infusion at low, median and high dose level BIBW 2992 medium dose plus three dose levels (low, medium and high) of cetuximab.

Results or absolute dosages were not disclosed.

SUMMARY OF THE INVENTION

A first object of the present invention is a method of treating patients suffering from cancers driven by deregulated Human Epidermal Growth Factor Receptor (HER/Human EGFR) comprising administering to a patient in need of such treatment a flexible and active regimen for combining an irreversible tyrosine kinase inhibitor (TKI) and a Human EGFR targeted monoclonal antibody (mAB), wherein in this method the TKI is administered according to a continuous regimen based on an average daily dose in the range of 10 to 50 mg and the mAB is co-administered according to a dosing regimen ranging from an average weekly iv dose of 50 to 500 mg/m$^2$ repeated thrice, twice or once a week, once in two weeks, once in three weeks or at least once monthly.

A second object of the invention is a pharmaceutical kit, comprising a first compartment which comprises an effective amount of a Human EGFR targeted mAB and a second compartment which comprises an effective amount of an irreversible TKI.

A third object of the invention is an irreversible TKI for use in a method of treatment of a patient suffering from a cancer driven by deregulated Human Epidermal Growth Factor Receptor (HER/Human EGFR) by coadministration with a Human EGFR targeted mAB, wherein the TKI is administered according to a continuous regimen based on an average daily dose in the range of 10 to 50 mg and the mAB is co-administered according to a dosing regimen ranging from an average weekly iv dose of 50 to 500 mg/m$^2$ repeated thrice, twice or once a week, once in two weeks, once in three weeks or at least once monthly to a patient in need of such treatment.

A fourth object of the invention is the use of an irreversible TKI for preparation of a pharmaceutical kit for treatment of patients suffering from cancers driven by deregulated Human Epidermal Growth Factor Receptor (HER/Human EGFR), comprising a first compartment which comprises an effective amount of a Human EGFR targeted mAB and a second compartment which comprises an effective amount of an irreversible TKI, wherein the TKI is to be administered according to a continuous regimen based on an average daily dose in the range of 10 to 50 mg and the mAB is to be co-administered according to a dosing regimen ranging from an average weekly iv dose of 50 to 500 mg/m$^2$ repeated thrice, twice or once a week, once in two weeks, once in three weeks or at least once monthly to a patient in need of such treatment.

DETAILED DESCRIPTION OF THE INVENTION

Supported by clinical results it has surprisingly been found that the combination of an irreversible TKI with Human EGFR targeted mAB has significantly more activity than may have been expected, based on the results reported in the prior art, i.e. that dual targeting of gefitinib/cetuximab or erlotinib/cetuximab is not active for treatment of patients with lung adenocarcinoma and acquired resistance to reversible TKIs, as well as in view of the low tolerability reported for such combinations or based on preclinical data.

The irreversible TKI and the mAB can be combined with good tolerability at the recommended doses of the individual drugs—which was not expected in view of the low activity and tolerability of the gefitinib/cetuximab or erlotinib/cetuximab combination reported by S. Ramalingam et al., Journal of Thoracic Oncology Vol. 3, Number 3, March 2008, 258-265 and by Y. Y. Janjigian et al., Clin Cancer Res 2011, 17: 2521-2527, summarized hereinbefore.

Clinical trial data support that the activity of the combinations according to the invention is NOT restricted to T790M mediated resistance to TKI treatment, i.e. not only overcomes T790M mediated (T790M+: tumor harboring T790M) acquired resistance to TKI treatment but also acquired resistance not caused by T790M (T790M−: tumor not harboring T790M), e.g. acquired resistance caused by other mechanisms such as MET oncogene or by unknown origin. There is no evidence in the prior art indicating that this may be the case.

These findings suggest that the combination treatment according to the invention has the potential for significant improvement of the therapeutic index for EGFR directed treatments of cancers driven by deregulated Human Epidermal Growth Factor Receptor (HER/Human EGFR), e.g. epithelial cell cancers. Any of these findings are supported by clinical results obtained with the combination of BIBW 2992 with cetuximab.

Patients suffering from cancers driven by deregulated Human Epidermal Growth Factor Receptor (HER/Human EGFR) include, without limitation, patients suffering from non-small cell lung cancer (NSCLC), head and neck squamous cell carcinoma (HNSCC), malignant glioma, breast cancer, esophageal cancer, gastric cancer, renal cancer, cervical cancer, prostate cancer, ovarian cancer, pancreatic cancer, hepatocellular cancer, and colorectal cancer (CRC), including metastatic forms thereof. Preferred indications are NSCLC and HNSCC, especially NSCLC.

Furthermore, patients having one of cancer indications specified hereinbefore which may advantageously be treated by the method of the invention include the following patient populations:

(a) TKI naive cancer patients, wherein the treatment provides prevention or delay of resistance to TKI treatment, (b) patients with tumors expressing the wild-type EGFR, (c) patients with tumors expressing mutated forms of the EGFR, (d) patients previously treated with EGFR inhibitors, such as gefitinib or erlotinib afatinib, dacomitinib or others wherein the treatment provides to overcome primary or acquired resistance to EGFR inhibitors (e) patients with acquired resistance to treatment with TKIs such as gefitinib or erlotinib, afatinib, dacomitinib or others wherein the treatment provides to overcome resistance to TKI treatment, (g) patient populations with primary or acquired resistance caused by T790M (T790M+), wherein the i treatment provides to prevent or overcome resistance to TKI treatment, and (h) patient populations with primary or acquired resistance not caused by T790M (T790M−), e.g. by other mechanisms such as MET oncogene or by unknown origin, wherein the treatment provides to prevent or overcome resistance to TKI treatment.

Preferably, the following patient populations having one of the cancer indications specified hereinbefore may advantageously be treated by the method of the invention:
- (c) patients with tumors expressing mutated forms of the EGFR (EGFR+),
- (d) patients previously treated with EGFR inhibitors, such as gefitinib or erlotinib afatinib, dacomitinib or others wherein the treatment provides to overcome primary or acquired resistance to EGFR inhibitors,
- (e) patients with acquired resistance to treatment with TKIs, such as gefitinib or erlotinib, afatinib, dacomitinib or others, wherein the treatment provides to overcome resistance to TKI treatment,
- (g) patient populations with primary or acquired resistance caused by T790M (T790M+), wherein the treatment provides to prevent or overcome resistance to TKI treatment, and
- (h) patient populations with primary or acquired resistance not caused by T790M (T790M−), e.g. by other mechanisms such as MET oncogene or by unknown origin, wherein the treatment provides to prevent/overcome resistance to TKI treatment.

More preferred, the following patient populations having one of the cancer indications specified hereinbefore may advantageously be treated by the method of the invention:
- (c) patients with tumors harboring EGFR mutations in exons 19 and 21 associated with drug sensitivity (i.e., G719X, exon 19 deletion, L858R, L861Q),
- (e) patients with acquired resistance to treatment with TKIs, such as gefitinib or erlotinib, afatinib, dacomitinib or others, wherein the treatment provides to overcome resistance to TKI treatment,
- (g) patient populations with primary or acquired resistance caused by T790M (T790M+), wherein the treatment provides to prevent or overcome resistance to TKI treatment, and
- (h) patient populations with primary or acquired resistance not caused by T790M (T790M−), e.g. by other mechanisms such as MET oncogene or by unknown origin, wherein the treatment provides to prevent or overcome resistance to TKI treatment.

Most preferred, the following patient population having one of the cancer indications specified hereinbefore may advantageously be treated by the method of the invention:
- (h) patient populations with primary or acquired resistance not caused by T790M (T790M−), e.g. by other mechanisms such as MET oncogene or by unknown origin, wherein the treatment provides to prevent or overcome resistance to TKI treatment.

Particularly preferred, the following patient population having one of the cancer indications specified hereinbefore may advantageously be treated by the method of the invention:
- (h') patient populations with acquired resistance not caused by T790M (T790M−), e.g. by other mechanisms such as MET oncogene or by unknown origin, wherein the treatment provides to overcome resistance to TKI treatment.

Irreversible TKIs suitable with regard to any aspects of the invention include, without limitation, EKB-569 (pelitinib), HKI-272 (neratinib), HKI-357, CI-1033, BIBW 2992 or PF-00299804, and any salts, preferably pharmaceutically acceptable salts, hydrates or solvates thereof, including polymorphs. Preferred TKIs are BIBW 2992 and PF-00299804. Most preferred is BIBW 2992.

As a further alternative irreversible TKIs suitable with regard to any aspects of the invention include 1-(4-(4-(3,4-dichloro-2-fluorophenylamino)-7-methoxyquinazolin-6-yloxy)piperidin-1-yl)prop-2-en-1-one, WZ 3146, WZ 4002, WZ 8040, and any salts, preferably pharmaceutically acceptable salts, hydrates or solvates thereof, including polymorphs.

MABs suitable with regard to any aspects of the invention include, without limitation, cetuximab, panitumumab, zalutumumab, nimotuzumab, and matuzumab. Preferred mABs are cetuximab and panitumumab. Most preferred is cetuximab. A further mABs suitable with regard to any aspects of the invention is necitumumab.

Any of the irreversible TKIs and any of the mABs mentioned in the context of the invention may be combined with each other with regard to the specified aspects of the invention.

Specific combinations suitable with regard to all aspects of the invention are
EKB-569/cetuximab, EKB-569/panitumumab, EKB-569/zalutumumab, EKB-569/nimotuzumab, EKB-569/matuzumab,
HKI-272/cetuximab, HKI-272/panitumumab, HKI-272/zalutumumab, HKI-272/nimotuzumab, HKI-272/matuzumab, HKI-272/necitumumab,
HKI-357/cetuximab, HKI-357/panitumumab, HKI-357/zalutumumab, HKI-357/nimotuzumab, HKI-357/matuzumab,
CI-1033/cetuximab, CI-1033/panitumumab, CI-1033/zalutumumab, CI-1033/nimotuzumab, CI-1033/matuzumab,
BIBW 2992/cetuximab, BIBW 2992/panitumumab, BIBW 2992/zalutumumab, BIBW 2992/nimotuzumab, BIBW 2992/matuzumab, BIBW 2992/necitumumab,
PF-00299804/cetuximab, PF-00299804/panitumumab, PF-00299804/zalutumumab, PF-00299804/nimotuzumab, PF-00299804/necitumumab, and PF-00299804/matuzumab.

Preferred combinations of the irreversible TKIs and the mABs suitable with regard to all aspects of the invention are
HKI-272/cetuximab, HKI-272/panitumumab, HKI-272/zalutumumab, HKI-272/nimotuzumab, HKI-272/matuzumab,
BIBW 2992/cetuximab, BIBW 2992/panitumumab, BIBW 2992/zalutumumab, BIBW 2992/nimotuzumab, BIBW 2992/matuzumab,
PF-00299804/cetuximab, PF-00299804/panitumumab, PF-00299804/zalutumumab, PF-00299804/nimotuzumab, and PF-00299804/matuzumab.

More preferred combinations of the irreversible TKIs and the mABs suitable with regard to all aspects of the invention are
HKI-272/cetuximab, HKI-272/panitumumab,
BIBW 2992/cetuximab, BIBW 2992/panitumumab,
PF-00299804/cetuximab, and PF-00299804/panitumumab.

Most preferred combinations of the irreversible TKIs and the mABs suitable with regard to all aspects of the invention are
BIBW 2992/cetuximab, BIBW 2992/panitumumab,
PF-00299804/cetuximab, and PF-00299804/panitumumab,
specifically preferred is BIBW 2992/cetuximab.

The expressions "prevention", "prophylaxis", "prophylactic treatment" or "preventive treatment" used herein should be understood synonymous and in the sense that the risk to develop a condition mentioned herein is reduced. The expression "prevention or delay of resistance" or "to overcome resistance" in the context of the invention means that development of resistance to TKI treatment is either avoided or onset of resistance is delayed or already existing (primary or acquired) resistance is overcome by the combination treatment regimen of the invention, reflected statistically by reduced incidence or later onset of resistance within a first patient population treated with a combination treatment regimen according to the invention, in comparison to an equivalent second patient population receiving parallel treatment but without the Human EGFR targeted monoclonal antibody component.

Resistance to TKI or EGFR inhibitor treatment means that the patient does not show a response to the treatment. This includes primary resistance of TKI naive patients when treated for the first time with a TKI, and acquired resistance of patients showing response under TKI treatment for a certain period of time but then progression of the disease again.

Furthermore, prevention or delay of resistance to TKI treatment means that the patients of the first patient population show response under the combination treatment regimen according to the invention either continuously or for a longer period of time, compared to the second patient population. Treatment response and progression of the disease are evaluated under the criteria laid down in the revised RECIST guideline (version 1.1). Eur J Cancer 2009; 45:228-247 mentioned hereinbefore.

A preferred embodiment of the first object of the present invention is a method of treating patients suffering from NSCLC, HNSCC, malignant glioma, breast cancer, esophageal cancer, gastric cancer, renal cancer, cervical cancer, prostate cancer, ovarian cancer, pancreatic cancer, hepatocellular cancer or CRC, including metastatic forms thereof, wherein in this method a TKI selected from the group consisting of EKB-569, HKI-272, HKI-357, CI-1033, BIBW 2992 and PF-00299804, or a pharmaceutically acceptable salt thereof, is administered according to a continuous regimen based on an average daily dose in the range of 10 to 50 mg and a mAB selected from the group consisting of cetuximab, panitumumab, zalutumumab, nimotuzumab and matuzumab is co-administered according to a dosing regimen ranging from an average weekly iv dose of 50 to 500 mg/m$^2$ repeated thrice, twice or once a week, once in two weeks, once in three weeks or at least once monthly to (c) a patient with a tumor expressing mutated forms of the EGFR, or (d) a patient previously treated with EGFR inhibitors, such as gefitinib or erlotinib afatinib, dacomitinib or others wherein the method provides to overcome primary or acquired resistance to EGFR inhibitors, (e) a patient with acquired resistance to treatment with TKIs such as gefitinib or erlotinib, afatinib, dacomitinib or others wherein the method provides to overcome resistance to TKI treatment, (g) a patient with primary or acquired resistance caused by T790M (T790M+), wherein the method provides to prevent or overcome resistance to TKI treatment, or (h) a patient with primary or acquired resistance not caused by T790M (T790M−), e.g. by other mechanisms such as MET oncogene or by unknown origin, wherein the method provides to prevent or overcome resistance to TKI treatment.

A further preferred embodiment of the first object of the present invention is a method of treating patients suffering from NSCLC, HNSCC, malignant glioma, breast cancer or CRC, including metastatic forms thereof, wherein in this method a TKI selected from the group consisting of HKI-272, BIBW 2992 and PF-00299804, (BIBW 2992 and PF-00299804 being especially preferred), or a pharmaceutically acceptable salt thereof, is administered according to a continuous regimen based on an average daily dose in the range of 10 to 50 mg and a mAB selected from the group consisting of cetuximab and panitumumab, is co-administered according to a dosing regimen ranging from an average weekly iv dose of 50 to 500 mg/m$^2$ repeated twice or once a week or once in two weeks to (c) a patient with a tumor harboring EGFR mutations in exons 19 and 21 associated with drug sensitivity (i.e., G719X, exon 19 deletion, L858R, L861Q), or (e) a patient with acquired resistance to treatment with TKIs such as gefitinib or erlotinib, afatinib, dacomitinib or others wherein the method provides to overcome resistance to TKI treatment, (g) a patient with primary/acquired resistance caused by T790M (T790M+), wherein the method provides to prevent or overcome resistance to TKI treatment, or (h) a patient with primary or acquired resistance not caused by T790M (T790M−), e.g. by other mechanisms such as MET oncogene or by unknown origin, wherein the method provides to prevent or overcome resistance to TKI treatment.

A further preferred embodiment of the first object of the present invention is a method of treating patients suffering from NSCLC or HNSCC, including metastatic forms thereof, wherein in this method a TKI selected from the group consisting of BIBW 2992 and PF-00299804 (BIBW 2992 being especially preferred), or a pharmaceutically acceptable salt thereof, is administered according to a continuous regimen based on an average daily dose in the range of 10 to 50 mg and a mAB selected from the group consisting of cetuximab and panitumumab (cetuximab being especially preferred), is co-administered according to a dosing regimen ranging from an average weekly iv dose of 50 to 500 mg/m$^2$ repeated twice or once a week or once in two weeks to (e) a patient with acquired resistance to treatment with TKIs, such as gefitinib or erlotinib, afatinib, dacomitinib or others, wherein the method provides to overcome resistance to TKI treatment, (g) a patient with primary or acquired resistance caused by T790M (T790M+), wherein the method provides to prevent or overcome resistance to TKI treatment, or (h) a patient with primary or acquired resistance not caused by T790M (T790M−), e.g. by other mechanisms such as MET oncogene or by unknown origin, wherein the method provides to preventor overcome resistance to TKI treatment.

A further preferred embodiment of the first object of the present invention is a method of treating patients suffering from NSCLC, including metastatic forms thereof, wherein in this method BIBW 2992, or a pharmaceutical acceptable salt thereof, is administered according to a continuous regimen based on an average daily dose in the range of 10 to 50 mg and cetuximab is co-administered according to a dosing regimen ranging from an average weekly iv dose of 50 to 500 mg/m$^2$ repeated twice or once a week to (h) a patient with primary or acquired resistance not caused by T790M (T790M−), e.g. by other mechanisms such as MET oncogene or by unknown origin, wherein the method provides to prevent or overcome resistance to TKI treatment, but most preferably to
(h') a patient with acquired resistance not caused by T790M (T790M−), e.g. by other mechanisms such as MET oncogene or by unknown origin, wherein the method provides to overcome resistance to TKI treatment.

A first preferred embodiment of the second object of the invention is a pharmaceutical kit, wherein the second compartment comprises an effective amount of a TKI selected from the group consisting of EKB-569 (pelitinib), HKI-272 (neratinib), HKI-357, CI-1033, BIBW 2992 and PF-00299804 or a pharmaceutically acceptable salt thereof.

A second preferred embodiment of the second object of the invention is a pharmaceutical kit, wherein the second compartment comprises an effective amount of a mAB selected from the group consisting of cetuximab, panitumumab, zalutumumab, nimotuzumab and matuzumab.

A second preferred embodiment of the second object of the invention is a pharmaceutical kit, wherein the second compartment comprises an effective amount of a mAB selected from the group consisting of cetuximab, panitumumab, zalutumumab, nimotuzumab and matuzumab.

A third preferred embodiment of the second object of the invention is a pharmaceutical kit, comprising a first compartment which comprises an effective amount of a mAB selected from the group consisting of cetuximab and panitumumab, and a second compartment which comprises an effective amount of a TKI selected from the group consisting of HKI-272, BIBW 2992 and PF-00299804, (BIBW 2992 and PF-00299804 being especially preferred), or a pharmaceutically acceptable salt thereof.

A fourth preferred embodiment of the second object of the invention is a pharmaceutical kit, comprising a first compartment which comprises an effective amount of a mAB selected from the group consisting of cetuximab and panitumumab (cetuximab being especially preferred), and a second compartment which comprises an effective amount of a TKI selected from the group consisting of BIBW 2992 and PF-00299804 (BIBW 2992 being especially preferred), or a pharmaceutically acceptable salt thereof.

A fifth preferred embodiment of the second object of the invention is a pharmaceutical kit, comprising a first compartment which comprises an effective amount of cetuximab, and a second compartment which comprises an effective amount of BIBW 2992, or a pharmaceutically acceptable salt thereof.

A first preferred embodiment of the third object of the invention is an irreversible TKI for use in a method of treatment of a patient suffering from NSCLC, HNSCC, malignant glioma, breast cancer, esophageal cancer, gastric cancer, renal cancer, cervical cancer, prostate cancer, ovarian cancer, pancreatic cancer, hepatocellular cancer or CRC, including metastatic forms thereof, by coadministration with a Human EGFR targeted mAB, wherein the TKI is selected from the group consisting of EKB-569, HKI-272, HKI-357, CI-1033, BIBW 2992 and PF-00299804, or a pharmaceutically acceptable salt thereof, and is administered according to a continuous regimen based on an average daily dose in the range of 10 to 50 mg, and
the mAB is selected from the group consisting of cetuximab, panitumumab, zalutumumab, nimotuzumab and matuzumab and is co-administered according to a dosing regimen ranging from an average weekly iv dose of 50 to 500 mg/m² repeated thrice, twice or once a week, once in two weeks, once in three weeks or at least once monthly to (c) a patient with a tumor expressing mutated forms of the EGFR, or
(d) a patient previously treated with EGFR inhibitors, such as gefitinib or erlotinib afatinib, dacomitinib or others wherein the method provides to overcome primary or acquired resistance to EGFR inhibitors,
(e) a patient with acquired resistance to treatment with TKIs such as gefitinib or erlotinib, afatinib, dacomitinib or others wherein the method provides to overcome resistance to TKI treatment,
(g) a patient with primary or acquired resistance caused by T790M (T790M+), wherein the method provides to prevent or overcome resistance to TKI treatment, or
(h) a patient with primary or acquired resistance not caused by T790M (T790M−), e.g. by other mechanisms such as MET oncogene or by unknown origin, wherein the method provides to prevent or overcome resistance to TKI treatment.

A second preferred embodiment of the third object of the invention is an irreversible TKI for use in a method of treatment of a patient suffering from NSCLC, HNSCC, malignant glioma, breast cancer or CRC, including metastatic forms thereof, wherein in this method
the TKI is selected from the group consisting of HKI-272, BIBW 2992 and PF-00299804, (BIBW 2992 and PF-00299804 being especially preferred), or a pharmaceutically acceptable salt thereof, and is administered according to a continuous regimen based on an average daily dose in the range of 10 to 50 mg, and
the mAB is selected from the group consisting of cetuximab and panitumumab, and is co-administered according to a dosing regimen ranging from an average weekly iv dose of 50 to 500 mg/m² repeated twice or once a week or once in two weeks to
(c) a patient with a tumor harboring EGFR mutations in exons 19 and 21 associated with drug sensitivity (i.e., G719X, exon 19 deletion, L858R, L861Q), or
(e) a patient with acquired resistance to treatment with TKIs such as gefitinib or erlotinib, afatinib, dacomitinib or others wherein the method provides to overcome resistance to TKI treatment,
(g) a patient with primary/acquired resistance caused by T790M (T790M+), wherein the method provides to prevent or overcome resistance to TKI treatment, or
(h) a patient with primary or acquired resistance not caused by T790M (T790M−), e.g. by other mechanisms such as MET oncogene or by unknown origin, wherein the method provides to prevent or overcome resistance to TKI treatment.

A third preferred embodiment of the third object of the invention is an irreversible TKI for use in a method of treatment of a patient suffering from NSCLC or HNSCC, including metastatic forms thereof, wherein in this method
the TKI is selected from the group consisting of BIBW 2992 and PF-00299804 (BIBW 2992 being especially preferred), or a pharmaceutically acceptable salt thereof, is administered according to a continuous regimen based on an average daily dose in the range of 10 to 50 mg, and
the mAB is selected from the group consisting of cetuximab and panitumumab (cetuximab being especially preferred), and is co-administered according to a dosing regimen ranging from an average weekly iv dose of 50 to 500 mg/m² repeated twice or once a week or once in two weeks to (e) a patient with acquired resistance to treatment with TKIs, such as gefitinib or erlotinib, afatinib, dacomitinib or others, wherein the method provides to overcome resistance to TKI treatment, (g) a patient with primary or acquired resistance caused by T790M (T790M+), wherein the method provides to prevent or overcome resistance to TKI treatment, or (h) a patient with primary or acquired resistance not caused by T790M (T790M−), e.g. by other mechanisms such as MET oncogene or by unknown origin, wherein the method provides to prevent or overcome resistance to TKI treatment.

A fourth preferred embodiment of the third object of the invention is an irreversible TKI for use in a method of treatment of a patient suffering from NSCLC, including metastatic forms thereof, wherein in this method the TKI is BIBW 2992, or a pharmaceutical acceptable salt thereof, and is administered according to a continuous regimen based on an average daily dose in the range of 10 to 50 mg, and the mAB is cetuximab and is co-administered according to a dosing regimen ranging from an average weekly iv dose of 50 to 500 mg/m$^2$ repeated twice or once a week to (h) a patient with primary or acquired resistance not caused by T790M (T790M−), e.g. by other mechanisms such as MET oncogene or by unknown origin, wherein the method provides to prevent or overcome resistance to TKI treatment, but most preferably to (h') a patient with acquired resistance not caused by T790M (T790M−), e.g. by other mechanisms such as MET oncogene or by unknown origin, wherein the method provides to overcome resistance to TKI treatment.

In a first preferred embodiment of the fourth object of the invention the irreversible tyrosine kinase inhibitor (TKI) is selected from the group consisting of EKB-569 (pelitinib), HKI-272 (neratinib), HKI-357, CI-1033, BIBW 2992 and PF-00299804 or a pharmaceutically acceptable salt thereof.

In a second preferred embodiment of the fourth object of the invention the Human EGFR targeted monoclonal antibody (mAB) is selected from the group consisting of cetuximab, panitumumab, zalutumumab, nimotuzumab, and matuzumab.

In a third preferred embodiment of the fourth object of the invention the cancer is selected from the group consisting of NSCLC, HNSCC, malignant glioma, breast cancer, esophageal cancer, gastric cancer, renal cancer, cervical cancer, prostate cancer, ovarian cancer, pancreatic cancer, hepatocellular cancer and CRC, including metastatic forms thereof, the TKI is selected from the group consisting of EKB-569, HKI-272, HKI-357, CI-1033, BIBW 2992 and PF-00299804, or a pharmaceutically acceptable salt thereof, the mAB is selected from the group consisting of cetuximab, panitumumab, zalutumumab, nimotuzumab and matuzumab, and the patient is (c) a patient with a tumor expressing mutated forms of the EGFR, or (d) a patient previously treated with EGFR inhibitors, such as gefitinib or erlotinib afatinib, dacomitinib or others wherein the method provides to overcome primary or acquired resistance to EGFR inhibitors, (e) a patient with acquired resistance to treatment with TKIs such as gefitinib or erlotinib, afatinib, dacomitinib or others wherein the method provides to overcome resistance to TKI treatment, (g) a patient with primary or acquired resistance caused by T790M (T790M+), wherein the method provides to prevent or overcome resistance to TKI treatment, or (h) a patient with primary or acquired resistance not caused by T790M (T790M−), e.g. by other mechanisms such as MET oncogene or by unknown origin, wherein the method provides to prevent or overcome resistance to TKI treatment.

In a fourth preferred embodiment of the fourth object of the invention the cancer is selected from the group consisting of NSCLC, HNSCC, malignant glioma, breast cancer and CRC, including metastatic forms thereof, the TKI is selected from the group consisting of HKI-272, BIBW 2992 and PF-00299804, (BIBW 2992 and PF-00299804 being especially preferred), or a pharmaceutically acceptable salt thereof, the mAB is selected from the group consisting of cetuximab and panitumumab, and is co-administered according to a dosing regimen ranging from an average weekly iv dose of 50 to 500 mg/m$^2$ repeated twice or once a week or once in two weeks to, and the patient is (c) a patient with a tumor harboring EGFR mutations in exons 19 and 21 associated with drug sensitivity (i.e., G719X, exon 19 deletion, L858R, L861Q), or (e) a patient with acquired resistance to treatment with TKIs such as gefitinib or erlotinib, afatinib, dacomitinib or others wherein the method provides to overcome resistance to TKI treatment, (g) a patient with primary/acquired resistance caused by T790M (T790M+), wherein the method provides to prevent or overcome resistance to TKI treatment, or (h) a patient with primary or acquired resistance not caused by T790M (T790M−), e.g. by other mechanisms such as MET oncogene or by unknown origin, wherein the method provides to prevent or overcome resistance to TKI treatment.

In a fifth preferred embodiment of the fourth object of the invention the cancer is selected from the group consisting of NSCLC or HNSCC, including metastatic forms thereof, the TKI is selected from the group consisting of BIBW 2992 and PF-00299804 (BIBW 2992 being especially preferred), or a pharmaceutically acceptable salt thereof, the mAB is selected from the group consisting of cetuximab and panitumumab (cetuximab being especially preferred), and the patient is (e) a patient with acquired resistance to treatment with TKIs, such as gefitinib or erlotinib, afatinib, dacomitinib or others, wherein the method provides to overcome resistance to TKI treatment, (g) a patient with primary or acquired resistance caused by T790M (T790M+), wherein the method provides to prevent or overcome resistance to TKI treatment, or (h) a patient with primary or acquired resistance not caused by T790M (T790M−), e.g. by other mechanisms such as MET oncogene or by unknown origin, wherein the method provides to prevent or overcome resistance to TKI treatment.

In a sixth preferred embodiment of the fourth object of the invention the cancer is NSCLC, including metastatic forms thereof, the TKI is BIBW 2992, or a pharmaceutical acceptable salt thereof, the mAB is cetuximab and is co-administered according to a dosing regimen ranging from an average weekly iv dose of 50 to 500 mg/m² repeated twice or once a week to (h) a patient with primary or acquired resistance not caused by T790M (T790M−), e.g. by other mechanisms such as MET oncogene or by unknown origin, wherein the method provides to prevent or overcome resistance to TKI treatment, In a seventh preferred embodiment of the fourth object of the invention (h') the patient has acquired resistance not caused by T790M (T790M−), e.g. by other mechanisms such as MET oncogene or by unknown origin, wherein the method provides to overcome resistance to TKI treatment.

Dosages/Irreversible TKI:

Dosage forms of the irreversible TKIs are either available on the market or described in publications. According to any aspect of the invention the TKI, e.g. BIBW 2992, is administered in a total average daily dose of 10 to 50 mg, e.g. in a total average daily dose selected from 10, 15, 20, 25, 30, 35, 40, 45 and 50 mg, optionally divided into multiple doses, e.g. 1, 2 or 3 doses to be administered through the day. Preferably the TKI is administered orally only once a time per day, but alternative routes of administration may be applied.

Dosages/mABs:

Dosage forms of the mABs also are either available on the market or described in publications. According to any aspect of the invention average weekly iv doses of 50 to 500 mg/m², e.g. 50, 75, 100, 200, 250, 300, 350, 375, 400, 425, 450, 475 and 500 mg/m² of the mAB component, e.g. cetuximab or panitumumab, may be applied in the regimen mentioned in the context of the invention.

Based on body weight single iv doses of 1 to 15 mg/kg, e.g. 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 mg/kg of the mAB component, e.g. cetuximab or panitumumab, may be applied in the regimen mentioned in the context of the invention. Based on a 70 kg adult patient this results in 70 to 1050 mg range for a single dose.

However, it may optionally be necessary to deviate from the dosage amounts specified for the TKI and/or the mAB component, within the limitations set, depending on the body weight or method of administration, the individual response to the medication, the nature of the formulation used and the time or interval over which it is administered. When dosages at the high end are administered it may be advisable to spread them over the day in a number of single doses.

Instruction for Coadministration:

Instructions for coadministration may be in any form suitable for pharmaceuticals, e.g. in form of a leaflet added to the dosage form within secondary packaging or an imprint on the primary or secondary packaging.

The following Example serve to illustrate the invention without restricting it:

Example 1

Activity and Tolerability of Afatinib (BMW 2992; A) and Cetuximab (C) in Patients with Non-Small Cell Lung Cancer (NSCLC) and Acquired Resistance to Erlotinib (E) or Gefitinib (G) (ClinicalTrials.gov Identifier: NCT01090011)

Background:

Despite initial responses to reversible EGFR-TKIs e.g. E or G, all NSCLC patients with EGFR sensitizing mutations experience disease progression. This "acquired resistance" (AR) is associated with a second site exon 20 EGFR T790M mutation (M) in over half of cases. So far, no therapy, including the anti-EGFR antibody C plus E, has proven effective in treating AR (Janjigian Y Y. Clin Cancer Res; Epub January 2011). Preclinical data suggest that A, a potent irreversible inhibitor of the ErbB receptor family, is active in M cell lines. Combined EGFR targeting with A and C has induced near complete responses in T790M transgenic murine models. This is the first clinical study to assess safety and preliminary efficacy of this combination in NSCLC patients.

Methods:

NSCLC patients with clinically defined AR (Jackman D. J Clin Oncol 2010; 28:357) received oral A 40 mg daily with escalating dose cohorts of biweekly C at 250 and 500 mg/m². Patients receiving the recommended phase 2 dose (RP2D) were evaluated for objective response. Acquisition of tumor tissue at or after emergence of AR was mandated.

Results:

Of 26 treated patients, 22 received the pre-defined maximum dose =RP2D: A 40 mg+C 500 mg/m². Median time on E or G at study entry was 2.4 years. No dose-limiting toxicity was observed. The common adverse events (AE) were rash (83%) and diarrhea (62%). 3 (6.4%) patients had grade 3 rash and 2 (4.3%) patients had grade 3 diarrhea. Disease control was observed in all patients enrolled at RP2D (tumor size reduction up to 76%, treatment duration up to 5+ months). Confirmed partial responses (PRs) were seen in 12/32 (38%) evaluable patients, including 10/17 (59%) and 5/55 (14%) not (yet) confirmed PRs in T790M+ and T790M− NSCLC, respectively.

Overall results regarding tolerability (adverse events) and treatment response are summarized in tables 1 and 2.

Conclusions:

Combined EGFR targeting with A and C is tolerable at the RP2D. Mild to moderate diarrhae and skin adverse events are manageable. Disease control was observed in all patients enrolled at RP2D. EGFRmut+ NSCLC with AR to erlotinib and gefitinib continues to depend on EGFR signaling. A in combination with C overcomes acquired resistance to prior erlotinib/gefitinib. The clinical activity is not restricted to T790M mediated acquired resistance.

TABLE 1

Rash/Acne and Diarrhae Adverse Events (AE) Summary

| AE | Afatinib 40 + 250 Cetux. | Afatinib 40 + 500 Cetux. | All |
|---|---|---|---|
| Rash/Acne, All grades | 4 (100.0) | 39 (83.0) | 43 (84.3) |
| Diarrhea, All grades | 2 (50.0) | 29 (61.7) | 31 (60.8) |
| Rash/Acne, Grade 3 | 0 (0.0) | 3 (6.4) | 3 (5.9) |
| Diarrhea, Grade 3 | 0 (0.0) | 2 (4.3) | 2 (3.9) |

(Afatinib 40 + 250 and 40 + 500 Cetux refers to the dosing regimen of Afatinib and Cetuximab, see Methods; 4(100.0) means 4 patients (100%)).

TABLE 2

Treatment Response by EGFR Mutation for patients at MTD (maximum tolerated dose)

| Response | T790M+ | T790M− | No Mutation | Un-informative | Total |
|---|---|---|---|---|---|
| Total Treated | 17 | 11 | 2 | 2 | 32 |
| CR [N(%)] | 0 (0.0) | 0 (0.0) | 0 (0.0) | 0 (0.0) | 0 (0.0) |
| PR [N(%)] | 10 (59%) | 6 (55%) | 0 (0.0) | 2 (100%) | 18 (56%) |
| PR [N(%)] confirmed | 6 (35%) | 4 (36%) | 0 (0) | 2 (100%) | 12 (38%) |
| SD [N(%)] | 7 (41.2) | 4 (36.4) | 2 (100.0) | 0 (0.0) | 13 (40.6) |
| PD [N(%)] | 0 (0.0) | 1 (9.1) | 0 (0.0) | 0 (0.0) | 1 (3.1) |

PR: partial response
SD: stable disease
PD: progressing disease
N: number of patients
T790M+: T790M positive patients
T790M+: T790M negative patients

The invention claimed is:

1. A method of treating a patient suffering from a non-small cell lung cancer (NSCLC) driven by deregulated Human Epidermal Growth Factor Receptor (HER/Human EGFR),
wherein: the patient has a tumor expressing mutated forms of the EGFR, and the patient has acquired resistance to tyrosine kinase inhibitor (TKI) treatment,
comprising administering to a patient in need of such treatment a flexible and active regimen for combining an irreversible tyrosine kinase inhibitor (TKI) and a Human EGFR targeted monoclonal antibody (mAB), wherein in this method the TKI is administered according to a continuous regimen based on an average daily dose in the range of 10 to 50 mg and the mAB is co-administered according to a dosing regimen ranging from an average weekly iv dose of 50 to 500 mg/m$^2$ repeated thrice, twice or once a week, once in two weeks, once in three weeks or at least once monthly,
wherein the method results in overcoming the acquired resistance to TKI treatment.

2. The method of claim 1, wherein
the TKI is selected from the group consisting of HKI-272, BIBW 2992 and PF-00299804, or a pharmaceutically acceptable salt thereof, and is administered according to a continuous regimen based on an average daily dose in the range of 10 to 50 mg,
the mAB is selected from the group consisting of cetuximab, panitumumab, zalutumumab, nimotuzumab and matuzumab and is co-administered according to a dosing regimen ranging from an average weekly iv dose of 50 to 500 mg/m$^2$ repeated thrice, twice or once a week, once in two weeks, once in three weeks or at least once monthly to:
a patient with a tumor expressing mutated forms of the EGFR,
and with acquired resistance to TKI treatment wherein the method results in overcoming resistance to TKI treatment.

3. The method of claim 1, wherein the cancer is NSCLC, HNSCC, including metastatic forms thereof,
the TKI is selected from the group consisting of BIBW 2992 and PF-00299804, or a pharmaceutically acceptable salt thereof, and is administered according to a continuous regimen based on an average daily dose in the range of 10 to 50 mg,
the mAB is selected from the group consisting of cetuximab and panitumumab, and is co-administered according to a dosing regimen ranging from an average weekly iv dose of 50 to 500 mg/m$^2$ repeated twice or once a week or once in two weeks to:
a patient with a tumor harboring EGFR mutations in exons 19 and 21 associated with drug sensitivity (i.e., G719X, exon 19 deletion, L858R, L861Q), and with acquired resistance to TKI treatment wherein the method results in overcoming resistance to TKI treatment.

4. The method of claim 1, wherein the cancer is NSCLC, including metastatic forms thereof,
the TKI is selected from the group consisting of BIBW 2992 and PF-00299804, or a pharmaceutically acceptable salt thereof, and is administered according to a continuous regimen based on an average daily dose in the range of 10 to 50 mg,
the mAB is selected from the group consisting of cetuximab and panitumumab, and is co-administered according to a dosing regimen ranging from an average weekly iv dose of 50 to 500 mg/m$^2$ repeated twice or once a week or once in two weeks to
(e) a patient with acquired resistance to treatment with TKIs, such as gefitinib or erlotinib, afatinib, dacomitinib or others, wherein the method provides to overcome resistance to TKI treatment, and
(g) with acquired resistance caused by T790M (T790M+), wherein the method results in overcoming resistance to TKI treatment, or
(h) with acquired resistance not caused by T790M (T790M−), e.g. by other mechanisms such as MET oncogene or by unknown origin, wherein the method results in overcoming resistance to TKI treatment.

5. The method of claim 1, wherein the cancer is NSCLC, including metastatic forms thereof,
the TKI is BIBW 2992, or a pharmaceutical acceptable salt thereof, and is administered according to a continuous regimen based on an average daily dose in the range of 10 to 50 mg,
the mAB is cetuximab and is co-administered according to a dosing regimen ranging from an average weekly iv dose of 50 to 500 mg/m$^2$ repeated twice or once a week to
(h) a patient with acquired resistance not caused by T790M (T790M−), wherein the method results in overcoming resistance to TKI treatment.

6. The method of claim 1, wherein
(g) the patient has acquired resistance caused by T790M (T790M+), and the method results in overcoming resistance to TKI treatment, or (h) the patient has acquired resistance not caused by T790M (T790M−), and the method results in overcoming resistance to TKI treatment.

7. The method of claim 1, wherein
(h) the patient has acquired resistance not caused by T790M (T790M−), and the method results in overcoming resistance to TKI treatment.

8. The method of claim 7, wherein the irreversible tyrosine kinase inhibitor (TKI) is selected from the group consisting of EKB-569 (pelitinib), HKI-272 (neratinib), HKI-357, CI-1033, BIBW 2992 and PF-00299804 or a pharmaceutically acceptable salt thereof.

9. The method of claim 7, wherein the TKI is selected from the group consisting of 1-(4-(4-(3,4-dichloro-2-fluorophenylamino)-7-methoxyquinazolin-6-yloxy)piperidin-1-yl)prop-2-en-1-one, WZ 3146, WZ 4002, and WZ 8040, or a pharmaceutical acceptable salt thereof.

10. The method of claim 8, wherein the Human EGFR targeted monoclonal antibody (mAB) is selected from the group consisting of cetuximab, panitumumab, zalutumumab, nimotuzumab and matuzumab.

11. The method of claim 8, wherein the Human EGFR targeted monoclonal antibody (mAB) is necitumumab.

12. The method of claim 2, wherein the acquired resistance to TKI treatment is acquired resistance of gefitinib, erlotinib, afatinib or dacomitinib treatment.

13. The method of claim 3, wherein the acquired resistance to TKI treatment is acquired resistance of gefitinib, erlotinib, afatinib or dacomitinib treatment.

14. The method of claim 5, wherein the acquired resistance not caused by T790M (T790M−) is caused by a MET oncogene mechanism or mechanism of unknown origin.

15. The method of claim 7, wherein the acquired resistance not caused by T790M (T790M−) is caused by a MET oncogene mechanism or mechanism of unknown origin.

16. The method of claim 1, wherein:
the TKI is selected from the group consisting of EKB-569 (pelitinib), HKI-272 (neratinib), HKI-357, CI-1033, BIBW 2992, PF-00299804, 1-(4-(4-(3,4-dichloro-2-fluorophenylamino)-7-methoxyquinazolin-6-yloxy)piperidin-1-yl)prop-2-en-1-one, WZ 3146, WZ 4002 and WZ 8040, or a pharmaceutically acceptable salt thereof, and
the mAB is selected from the group consisting of cetuximab, panitumumab, zalutumumab, nimotuzumab and matuzumab.

* * * * *